United States Patent [19]

Pezzoli et al.

[11] 4,385,077

[45] May 24, 1983

[54] ASBESTOS TREATMENT WITH METAL OXIDES

[75] Inventors: Paul A. Pezzoli; Stanley F. Spangenberg, both of Midland, Mich.

[73] Assignee: The Dow Chemical Company, Midland, Mich.

[21] Appl. No.: 12,933

[22] Filed: Feb. 16, 1979

Related U.S. Application Data

[63] Continuation of Ser. No. 756,206, Jan. 3, 1977, abandoned.

[51] Int. Cl.[3] .................................................. A61K 7/40

[52] U.S. Cl. ........................................ 427/2; 162/153; 427/215; 427/419.2; 428/271; 428/361; 428/389; 428/404; 428/443

[58] Field of Search ................... 427/215, 419 A, 301, 427/2, 217, 343; 428/443, 404, 389, 361, 379, 271; 162/153

[56] References Cited

U.S. PATENT DOCUMENTS

| | | | |
|---|---|---|---|
| 929,003 | 7/1909 | Norton | 162/153 |
| 2,661,288 | 12/1953 | Barbaras | 162/153 |
| 2,901,379 | 8/1959 | Shannon et al. | 428/389 |
| 2,949,358 | 8/1960 | Alexander et al. | 428/404 |
| 2,972,529 | 2/1961 | Alexander et al. | 428/404 |
| 3,189,563 | 6/1965 | Hauel | 427/419 A |
| 3,297,516 | 1/1967 | Naumann et al. | 162/153 |
| 3,372,051 | 3/1968 | Stalego | 427/343 |
| 3,849,181 | 11/1974 | Green | 428/390 |

*Primary Examiner*—Michael R. Lusignan
*Assistant Examiner*—Janyce A. Bell

[57] ABSTRACT

A method of treating asbestos comprising depositing on at least a portion of the asbestos a material consisting essentially of an oxide of at least one metal selected from the group consisting of first series transition metals, second series transition metals, and group II B metals.

2 Claims, No Drawings

ASBESTOS TREATMENT WITH METAL OXIDES

This is a continuation of application Ser. No. 756,206, filed Jan. 3, 1977 now abandoned.

BACKGROUND OF THE INVENTION

This invention relates to asbestos. More in particular, the present invention relates to a method of treating asbestos.

"Asbestos" is a general term applied to a group of naturally occurring fibrous silicate minerals that are commercially important because of their fibrous characteristics. Four principal types of asbestos minerals generally enter world commerce. These are chrysotile, crocidolite, amosite and anthophyllite. Of these, chrysotile is perhaps the most important, accounting for about 95 percent of the world's asbestos production.

Chemically, chrysotile asbestos is the fibrous form of the mineral serpentine, a hydrated magnesium silicate having the general formula $Mg_3Si_2O_3(OH)_4$. Structurally the chrysotile asbestos is believed to consist of rolled up sheets formed from two layers. The first layer is a continuous network of silica ($SiO_2$) tetrahedra. This layer is interlocked through common oxygen atoms with a second layer of magnesium hydroxide ($Mg(OH_2)$) octahedra. The walls of the asbestos fibers are composed of a number of such individual sheets contorted into scrolls with the magnesium hydroxide layer on the outside. Consequently, one of the dominant chemical features of chrysotile asbestos is its alkaline surface characteristics.

The surface modification of asbestine minerals, such as chrysotile, has attracted a good deal of attention from research workers during recent years. A large number of surface treatment methods have been proposed and evaluated for the purpose of modifying certain predetermined properties of the asbestos fibers. These procedures include: coating the surface of asbestos fibers with a phosphate, polyphosphate, or corresponding acid to improve the filtration characteristic of the fibers (U.S. Pat. Nos. 3,535,150, 3,957,571); treating asbestos fibers with magnesium carbonate or an oxide of a polyvalent metal to enhance the tensile strength of the fibers (U.S. Pat. Nos. 1,982,542; 2,451,805; 2,460,734); coating an asbestos fabric with an insoluble inorganic oxide to render the fabric flame resistant and water repellent (U.S. Pat. No. 2,406,779); mixing a detergent organic surface-active agent with fibrous asbestos agglomerates to disperse the asbestos fibers (U.S. Pat. No. 2,626,213); and distributing small amounts of polymeric particles or a water-soluble macro-molecular organic substance throughout an asbestos product to reduce dust emitted by the asbestos during handling and use (U.S. Pat. Nos. 3,660,148; 3,967,043).

An area of concern to the producers and users of asbestine material has been the potential health problems allegedly associated with asbestos exposure. It has been reported by the National Safety Council that persons who inhale large amounts of asbestos dust can develop disabling or fatal pulmonary and pleural fibrosis (asbestosis) and several types of malignancy of the respiratory tract ("Asbestos," *National Safety Council Newsletter,* R & D Section, June 1974). There is also speculation that asbestos may cause various forms of carcinogenesis, particularly carcinoma of the lung, pleura and peritoneum (R. F. Holt, "Asbestosis," *Nature,* 253, 85 (1975)). Since the pathogenicity of asbestos minerals is apparently unmatched by any other silicate, there has been much interest in developing a method of passivating asbestos to reduce any potential fibrogenic and carcinogenic effects on those exposed to it without adequate precaution.

Existing methodology for studying the in vivo fibrogenic effects of asbestos involves direct inhalation or intratracheal administration of asbestos fibers to animals. Subsequently, the experimentally treated animals are examined, usually months later, for pathological and histochemical evidence of fibrosis. Since the incubation period for asbestos-induced diseases is reported to be unusually long, experiments of this type are complicated, expensive and time consuming.

However, recent work done by R. R. Hefner, Jr. and P. J. Gehring (*American Industrial Hygiene Association Journal,* 36, 734–740 (1975)) shows that a relationship exists between the in vivo fibrogenicity of asbestos and its in vitro hemolytic activity. Hemolytic activity, or hemolysis, is a measure of induced blood cell rupture when fibers are agitated with a suspension of blood erythrocytes. Numerous other authors have also made similar in vitro evaluations of a number of particulates.

The in vitro hemolytic model provides a rapid, relatively inexpensive test which reliably assesses the fibrogenic potential of asbestos. Consequently, the hemolytic model has been employed in the present invention to test the effectiveness of certain asbestos treating procedures found to be potentially useful in alleviating some of the health problems reportedly associated with asbestos fibers.

Various materials have been examined which interact with the surface of asbestos fibers and reduce its hemolytic activity. Such material includes disodium ethylenediamine tetraacetic acid (EDTA), simple phosphates, disodium versenate, polyvinylpyridine N-oxide and aluminum (G. Macnab and J. S. Harington, *Nature* 214, 522–3 (1967), and certain acidic polymers (R. J. Schnitzer and F. L. Pundsack, *Environmental Research* 3, 1–14 (1970). In addition, West German Pat. No. 1,642,022 discloses that asbestos coated with polyvinylpyridine N-oxide minimizes the risk of asbestosis.

Some of these known materials, such as EDTA, are solubilized in body fluids and do not reduce the long term hemolytic activity of the asbestos. There is therefore a need to determine materials which will adhere to the asbestos and reduce its hemolytic activity. Such passivating materials should not adversely affect the useful commercial properties of the asbestos.

SUMMARY OF THE INVENTION

The present invention is a method for treating asbestos comprising depositing on at least a portion of the asbestos a material consisting essentially of an oxide of at least one metal selected from the group consisting of first series transition metals, second series transition metals, and group II B metals.

Using a hemolysis test described herein, as an in vitro screening test to assess the effectiveness of the metal oxide treatment, it has been surprisingly found that asbestos fibers with at least one metal oxide deposited thereon have reduced hemolytic activity in comparison with untreated asbestos fibers.

DESCRIPTION OF THE PREFERRED EMBODIMENT

In accordance with the present invention, asbestos is treated to deposit at least one metal oxide selected from the group consisting of first series transition metals, second series transition metals and group II B metals on at least a portion of the asbestos.

A number of suitable deposition techniques can be employed to treat the asbestos. For example, the asbestos can be contacted with a solution of an ionizable salt of at least one metal, to react the ionizable salt with surface-adsorbed water molecules on the asbestos, thereby precipitating an oxide of at least one of the metals on at least a portion of the surface of the asbestos.

Alternatively, the metal oxide can be deposited on the asbestos by directly contacting the surface of the asbestos with a suspension of at least one metal oxide in a liquid medium, such as water. One suitable technique involves suspending a particulate metal oxide in water, spraying the suspension onto the surface of the asbestos and removing the water by drying. Metal oxides which can be suitably applied in this manner include those that are insoluble in the suspending medium.

In another embodiment, the asbestos can be contacted with a gaseous mixture of a volatile ionizable metal salt and an inert gas. Suitable ionizable metal salts are those that can be volatilized into a gas at room temperature, such as tin tetrachloride, titanium tetrachloride, or the like. Suitable inert gases are defined as those that are substantially unreactive with both the ionizable metal salt and with the asbestos, for example, nitrogen.

For the purposes of this specification, the following definitions are adopted. The first series of transition metals begins with element number 21, scandium, and continues through element number 29, copper. The second series of transition metals begins with yttrium, number 39, and ends with silver 47. The group II B metals are zinc, cadmium, and mercury. The oxidation state (valence) of metals which commonly exhibit more than one valence is indicated by a Roman numeral in parentheses following the metal to which it refers. The terms "ionizable salt" and "metal oxide" refer to both the anhydrous and hydrated forms of those compounds.

The methods of treating the asbestos include contacting the asbestos with an ionizable salt of at least one suitable metal on at least a portion of the asbestos. In this context an ionizable salt is defined as a salt which dissociates spontaneously into cations and anions when dissolved in a suitable polar solvent, such as water, formamide, acetamide, ethanol, 1-propanol, dimethyl sulfoxide, methanol, mixtures thereof, and the like. The preferred solvent is water.

Any first series transition metal, second series transition metal, or group II B metal cation which is capable of forming an oxide can be used.

Preferably, the first series transition metal is selected from the group consisting of titanium (IV), chromium, manganese, iron (III), cobalt, and nickel; the second series transition metal is yttrium; and the group II B metal is cadmium. Most preferably, the metal cation is titanium (IV).

Any ionizable salt which will ionize in solution to produce a cation of at least one of the above metal can be used in the present process. However, the preferred ionizable salt is a chloride, sulfate, nitrate, or a mixture thereof of at least one of the metals. More preferably, the ionizable salt is a water soluble chloride salt of at least one of the metals. Furthermore, the ionizable salt can contain more than one type of cation and one type of anion. For example, a mixture of chloride salts of two metals, or a mixture of the chloride and sulfate salts of the same metal is suitable.

The concentration of the solution of the ionizable salt employed in the present process is sufficient to allow the ionizable salt to react with at least a portion of the water molecules on the asbestos. Preferably, the concentration of the solution of the ionizable salt is from about 1 percent by weight of the salt to about the concentration corresponding to a saturated solution of the particular metal salt. For example, when nickel chloride hexahydrate is the ionizable salt, the concentration of the salt in an aqueous salt solution at 20° C. and 1 atmosphere pressure is from about 1 to about 72 percent by weight. More preferably, the concentration of the solution of the ionizable salt is from about 5 to about 10 percent by weight of the salt.

A number of suitable techniques are known for initially applying the ionizable salt solution compounds onto the asbestos. These techniques include spraying the ionizable salt solution onto the asbestos or soaking the asbestos in the ionizable salt solution. The preferred method of contacting the asbestos with the ionizable salt solution is by slurrying the asbestos in the ionizable salt solution for a sufficient time to allow the surface of the asbestos to be contacted and wetted by the solution.

Advantageously, the mixture of asbestos and the ionizable salt solution can then be agitated at temperatures of from about 25° C. to about 100° C. for a sufficient time to allow the ionizable salt solution to contact at least a portion, and preferably substantially all of the asbestos surfaces. The agitation of the mixture is accomplished by use of agitation means well-known in the art. These include mechanical, air, hydraulic or magnetic means for inducing agitation.

Following agitation, the asbestos fibers suspended in the ionizable salt solution can be separated from the filtrate (ionizable salt solution) by any suitable solid-liquid separation technique such as vacuum filtration. Preferably, the ionizable salt-treated asbestos is subsequently washed with a suitable solvent, such as deionized water, to remove any non-adherent salt compound. The asbestos can then be dried by any suitable technique, such as air drying, heating, vacuum and the like.

The asbestos treated by the present method is characterized as being a fibrous asbestos material consisting essentially of asbestos fibers with a coating of an oxide of at least one metal deposited on at least a portion of the asbestos fibers. The metal is selected from the group consisting of first series transition metals, second series transition metals, and group II B metals. Preferably, the asbestos material consists of asbestos fibers coated with substantially only a metal oxide.

The asbestos treated by the present invention can include chrysotile, crocidolite, amosite, or anthophyllite asbestos. Chrysotile, being the most abundant type of asbestos, is the preferred material for treatment by the present process. The physical form of asbestos treated includes fibrous mineral bundles of fine crystalline fibers, or individual fibers. Preferably the asbestos is in the form of bundles of crystalline fibers. Generally, the individual fibers of the bundle have a fiber length of at least about 0.5 micron, and a diameter of at least about 0.01 micron. However, other fiber lengths and diameters can be employed.

The exact mechanism by which the metal oxide forms an adherent coating on the asbestos is not completely understood. It is believed that the coating is due to the alkaline outer surface of the asbestos fiber. The individual fibers are composed of a network of magnesium hydroxide tetrahedra. The outermost portion of the tetrahedra contains hydroxyl groups and surface adsorbed water molecules. There is some evidence that hydroxyl hydrogens are being displaced by the metal cation, to form a bond between the metal and asbestos. Since each asbestos fiber is composed of a number of individual sheets having outer hydroxyl groups, and because these sheets are contorted into concentric scrolls, the deposition of the metal oxide may occur on more than just the outermost exposed surface of the asbestos fiber. Some of the metal oxide may impregnate the interior scrolls of the fiber and deposit on the interior surface.

Any amount of metal oxide is beneficial to reduce hemolysis. However, the metal oxide that is deposited on the asbestos is preferably present in an amount of from about 0.05 to about 5.0 percent by weight based on the weight of the asbestos. The metal oxide deposited on the exposed asbestos surface is from about 0.5 to about 250 angstroms thick. Preferably, the oxide surface coating is from about 2 to about 50 angstroms thick. As recognized by those skilled in the art, the thickness of the surface coating can vary depending on the nature of the asbestos, its intended end use, and economics.

The following examples further illustrate the present process.

EXAMPLES

A regular grade of Carey 7RF-9 Canadian chrysotile asbestos was used in all of the following examples. The asbestos has a mean fiber length of about 30 microns, and contained about 10–15 percent by weight of impurities. The impurities present were characterized by X-ray diffraction and were found to be about 5 percent by weight $Fe_3O_4$, about 5–10 percent by weight $Mg(OH)_2$ and fractional weight percents of minor impurities generally associated with commercially pure chrysotile asbestos, such as aluminum, chromium, cobalt, scandium and the like.

EXAMPLE 1

Two grams (g) of the asbestos were placed in a glass tube which has a gas inlet at both ends. The glass tube was placed on a rolling mill and allowed to rotate so that the asbestos contained within the tube was free to tumble and agitate. Anhydrous nitrogen gas was bubbled through an aqueous solution of $TiCl_4$ at a rate of from about 50 to about 150 cubic centimeters per minute. The resultant metal halide-saturated nitrogen was passed over the tumbling asbestos fibers. When unreacted $TiCl_4$ was observed exiting from the exhaust gas outlet of the tube, the asbestos fibers were removed from the reaction tube.

The resulting chrysotile surface coating on the fibers was characterized by X-ray diffraction and atomic absorption spectroscopy. A coating of titanium (IV) oxide was shown to be distributed along the surface of the asbestos fibers. Both electron emission spectroscopy and atomic absorption spectroscopy were used to determine the amount of vapor-deposited oxide on the fibers. The results verified microscopy data in that about 3 angstroms of titanium oxide were coated on the fibers. High magnification transmission electron microscopy indicated no significant morphological differences between uncoated and coated fibers.

Since chrysotile asbestos is widely used for high temperature insulation, the thermal stability of the coated asbestos was investigated. The differential thermal analysis of coated and uncoated asbestos indicated that there was no appreciable difference in thermal stability due to the coating.

Hemolysis tests of the coated asbestos fibers were conducted in the following manner: Whole rat blood was suspended in 200–300 ml of ISOTON®, an isotonic blood cell diluent, without an anticoagulant. The whole blood suspension was centrifuged and the red cells were collected and washed in 200–300 ml volume of the pure isotonic diluent. The washing removed plasma which is known to inhibit blood hemolysis from the whole blood suspension. After subsequent centrifugation of the washed cell suspension, a final blood suspension was prepared. This suspension was a 2 percent, by volume, concentration of centrifuged red blood cells in the isotonic diluent.

About 250 milligrams (mg) asbestos fibers were placed in tissue culture flasks and a 25 ml volume of the 2 percent blood suspension was added to each flask. The resultant mixture was agitated by mechanical means and placed in a constant temperature (98.6±0.5° F.) water bath. The flasks were incubated for 30 minutes in a mechanical shaking incubator at a slow, constant rate of 50 cycles per minute. Control blood suspensions were incubated using the same procedure. Spontaneous hemolysis was determined by incubating the 2 percent blood suspension without asbestos fibers. A 100 percent hemolyzed sample was prepared by adding to the 2 percent blood suspension a small amount (less than one mg) of saponin powder (a known hemolytic agent).

The culture flasks were removed from the incubator after 30 minutes and the contents of each flask were centrifuged. A 3 ml volume of the resultant supernatant liquid was withdrawn and diluted with deionized water to a volume of 100 ml. The absorbance of the diluted samples was measured at 415 nanometer (nm) using a double-beam spectrophotometer. The diluted spontaneous hemolysis liquid was used as the reference solution in all absorbance measurements. Percent hemolysis was defined as $$\%\ \text{Hemolysis} = \frac{A_H}{A_{100}} \times \frac{100}{100}$$

where $A_H$ was the absorbance of a sample with asbestos fibers and $A_{100}$ was the absorbance of the 100% hemolyzed sample.

The dramatic reduction of hemolytic activity induced by the deposited titanium (IV) oxide is shown in Table I.

EXAMPLE 2

One gram (g) of the asbestos was placed in a 50 milliliters (ml) flask at 20° C. and 1 atmosphere pressure. To this was added 20 ml of an aqueous $FeCl_3.6H_2O$ solution containing 10 percent by weight $FeCl_3.6H_2O$.

The resultant slurry was agitated by use of a magnetic stirring bar to insure uniform dispersion of the $FeCl_3.6H_2O$ throughout the asbestos fibers. Agitation of the slurry in this manner was maintained at 25°–70° C. for about 60 minutes. The slurry was then filtered by vacuum filtration using Whatman #1 filter paper and a porcelain Buchner funnel. The filtered asbestos fibers were washed with 500 ml of deionized water to remove any undeposited salts and allowed to air dry at room temperature for from 12 to 15 hours.

The chrysotile surface coating was characterized by X-ray diffraction and atomic absorption spectroscopy. A coating of iron (III) oxide was shown to be distributed along the surface of the asbestos fibers. Both electron emission spectroscopy and atomic absorption spectroscopy were used to determine the amount of oxide coating on the fibers. The results verified microscopy data in that about 1 angstrom of iron (III) oxide was coated on the fibers. High magnification transmission electron microscopy indicated no significant morphological differences between uncoated and coated fibers.

The reduction of hemolytic activity induced by the deposited iron (III) oxide is shown in Table I.

EXAMPLES 3-9

Examples 3-9 were prepared in substantially the same manner as described in Example 2, except that the salt of different metals was used in the initial contacting step. The reduction of hemolytic activity induced by the deposited metal oxides is shown in Table I.

COMPARATIVE EXAMPLE A

Uncoated chrysotile asbestos was tested for hemolytic activity by the method described in Example 1. The results are shown in Table I.

TABLE I

Hemolysis Induced by Oxide Coating On Chrysotile Asbestos

| Example | Coating | % Hemolysis |
|---|---|---|
| 1 | $TiO_2$ | 1 |
| 2 | $Fe_2O_3.xH_2O$ | 3 |
| 3 | $Y_2O_3.xH_2O$ | 7 |
| 4 | $Mn_3O_4.xH_2O$ | 13 |
| 5 | $TiO_2.xH_2O$ | 14 |
| 6 | $Cr_2O_3.xH_2O$ | 16 |
| 7 | $NiO.xH_2O$ | 17 |
| 8 | $CdO.xH_2O$ | 22 |
| 9 | $CoO.xH_2O$ | 25 |
| A | None | 70 |

The durability of the coatings of Examples 1, 2, and A was determined by a series of attrition tests. The first-stage tests consisted of washing the coated asbestos fibers sequentially with (1) water, (2) an aqueous solution of 0.1 normal (N) HCl, (3) an aqueous solution of 0.1 N NaOH, and (4) acetone. Treated fibers were also tested for durability by heat treatment for 3 hours at 150° C. and by grinding in a mechanical blender. After each of the six tests, the coated fibers were re-evaluated using the hemolysis test. The results of first-stage attrition test are outlined in Table II. The durability of a coating in a test was indicated by the difference in the hemolysis value before and after attrition. An increase in the percent hemolysis, indicated that the coating was being removed by that test.

When the uncoated chrysotile was heated to 150° C. for three hours the hemolytic activity of the fibers was reduced from 70 percent to 12 percent as shown in Table II. The reduction in hemolytic activity of the uncoated asbestos as a function of temperature and time was studied. The results indicated that no passivation of the fibers occurred through heat treatment; instead, reversible dehydration of the fibers was observed.

TABLE II

First-Stage Attrition Tests with Coated Chrysotile Asbestos

| | | % Hemolysis | | | | | | |
|---|---|---|---|---|---|---|---|---|
| Example | Coating | Initial | $H_2O$ Wash | 0.1 N HCl Wash | 0.1 N NaOH Wash | Acetone Wash | Heated to 150° C./3 Hr | Ground |
| 1 | $TiO_2$ | 1 | 70 | 47 | 81 | 49 | 21 | 63 |
| 2 | $Fe_2O_3.xH_2O$ | 3 | 24 | 17 | 49 | 4 | 5 | 4 |
| A | None | 70 | 77 | 40 | 75 | 78 | 12 | 78 |

The results presented in Table I-II clearly indicate the significant reduction in hemolysis achieved by the present process. Untreated asbestos ruptured about 70% of the available red cells in a blood suspension while the various tungstate coated fibers induced from 1 to 25% hemolysis. Furthermore, the coatings on the chrysotile asbestos have been demonstrated to be durable when subjected to a series of chemical and physical tests.

What is claimed is:

1. A method of reducing the hemolytic activity of fibrous asbestos which is inhaled by humans or animals which comprises:

employing as the asbestos source fibrous asbestos the surfaces of which are coated with an effective amount of cadmium oxide whereby the hemolytic activity of the asbestos which is inhaled by humans or animals is reduced.

2. A method of reducing the hemolytic activity of fibrous asbestos which is inhaled by humans or animals which comprises:

employing as the asbestos source fibrous asbestos the surfaces of which are coated with an effective amount of chromium oxide or manganese peroxide whereby the hemolytic activity of the asbestos which is inhaled by humans or animals is reduced.

* * * * *